(12) United States Patent
Tong et al.

(10) Patent No.: US 9,326,928 B2
(45) Date of Patent: May 3, 2016

(54) THICK CLEANING COMPOSITION

(75) Inventors: Haiyang Tong, Jiangsu (CH); Jun Lu, Jiangsu (CN); Anjian Hui, Jiangsu (CN)

(73) Assignee: Suzhou Eleco Chemical Industry Co., Ltd. (CN)

( * ) Notice: Subject to any disclaimer, the term of this patent is extended or adjusted under 35 U.S.C. 154(b) by 175 days.

(21) Appl. No.: 13/989,007

(22) PCT Filed: Nov. 3, 2011

(86) PCT No.: PCT/CN2011/081712
§ 371 (c)(1),
(2), (4) Date: Jun. 6, 2013

(87) PCT Pub. No.: WO2012/068948
PCT Pub. Date: May 31, 2012

(65) Prior Publication Data
US 2013/0251648 A1    Sep. 26, 2013

(30) Foreign Application Priority Data

Nov. 22, 2010 (CN) .......................... 2010 1 0553162

(51) Int. Cl.
| | | |
|---|---|---|
| *A61K 8/92* | (2006.01) | |
| *A61K 8/18* | (2006.01) | |
| *A61Q 19/00* | (2006.01) | |
| *A61Q 19/10* | (2006.01) | |
| *A61K 8/44* | (2006.01) | |
| *A61K 8/34* | (2006.01) | |
| *A61K 8/36* | (2006.01) | |
| *A61K 8/37* | (2006.01) | |
| *A61Q 5/02* | (2006.01) | |
| *A61Q 11/00* | (2006.01) | |
| *A61Q 90/00* | (2009.01) | |

(52) U.S. Cl.
CPC ................. *A61K 8/442* (2013.01); *A61K 8/342* (2013.01); *A61K 8/361* (2013.01); *A61K 8/37* (2013.01); *A61K 8/44* (2013.01); *A61Q 5/02* (2013.01); *A61Q 11/00* (2013.01); *A61Q 19/10* (2013.01); *A61Q 90/00* (2013.01)

(58) Field of Classification Search
CPC ......... A61Q 19/00; A61Q 19/10; A61K 8/92; A61K 2300/00
See application file for complete search history.

(56) References Cited

U.S. PATENT DOCUMENTS

| | | | | |
|---|---|---|---|---|
| 5,153,340 | A | * 10/1992 | Ichikawa et al. | ............... 552/509 |
| 5,693,255 | A | * 12/1997 | Okamoto et al. | ............... 516/58 |
| 6,599,936 | B1 | * 7/2003 | Bajor et al. | ................... 514/532 |
| 2004/0266656 | A1 | * 12/2004 | Sakurai | ......................... 510/475 |
| 2005/0239669 | A1 | * 10/2005 | Krzysik et al. | ................ 510/130 |
| 2007/0213244 | A1 | 9/2007 | Tobita | |

FOREIGN PATENT DOCUMENTS

| | | |
|---|---|---|
| CN | 101018851 A | 8/2007 |
| CN | 102028627 A | 4/2011 |
| JP | S49-63683 | 6/1974 |
| JP | 03-275697 | 12/1991 |
| JP | 07-215831 | 8/1995 |
| JP | 2000-053524 | 2/2000 |
| JP | 2000-136114 | 5/2000 |
| JP | 2000-154112 | 6/2000 |
| JP | 2001-122742 | 5/2001 |
| JP | 2002265990 A | 9/2002 |
| JP | 2006-077184 | 3/2006 |
| JP | 2006-306849 | 11/2006 |
| JP | 2007-008884 | 1/2007 |
| JP | 2007-051167 | 3/2007 |
| JP | 2007-051168 | 3/2007 |
| JP | 2008-231346 | 10/2008 |
| WO | 2012068948 A1 | 5/2012 |

OTHER PUBLICATIONS

International Search Report dated Feb. 16, 2012 for International Application Serial No. PCT/CN2011/081712, International Filing Date Nov. 3, 2011 consisting of 5 pages.
English translation of Japanese Office Action for Japanese Serial No. 2013-539124 dated Sep. 8, 2014 consisting of 6 pages.

* cited by examiner

*Primary Examiner* — Frederick Krass
*Assistant Examiner* — Tracy Liu
(74) *Attorney, Agent, or Firm* — Christopher & Weisberg, P.A.

(57) ABSTRACT

A thick cleaning composition, comprising a long-chain fatty acyl acidic amino acid ester; a fatty compound of fatty acid, fatty alcohol, fatty alcohol ether or polyol fatty acid ester; a surfactant; a solvent composed of water, lower alcohol, polyol and polyol ether; and further comprising a beautifying and cleaning adjuvant for skin, eyes, teeth and hair. The cleaning composition can achieve satisfactory thick appearance when used for cleaning skin and hair, and maintain stable viscosity at different temperatures. In use, the composition can be easily daubed, and foams quickly with good foaming quality.

18 Claims, 3 Drawing Sheets

THICK CLEANING COMPOSITION

CROSS-REFERENCE TO RELATED APPLICATIONS

This application is a Submission Under 35 U.S.C. 371 for U.S. National Stage Patent Application of, and claims priority to, International Application Number PCT/CN2011/081712 entitled THICK CLEANING COMPOSITION, filed Nov. 3, 2011, which is related to and claims priority from Chinese Patent Number 201010553162.X, filed Nov. 22, 2010, the entirety of all of which are incorporated herein by reference.

FIELD OF THE INVENTION

The invention relates to a thick cleaning composition, in particular to a thick liquid crystal cleaning composition for cleaning skin, eyes, teeth and hair in the field of personal care products.

BACKGROUND OF THE INVENTION

Cleaning compositions for decontaminating and cleaning skin, eyes, teeth and hair generally contain various surfactants for the purpose of cleaning and decontamination. In order to further improve foaming and cleaning effects of a cleaning composition, more than one surfactant is often added. A certain amount of a solvent, especially water or a mixed solvent of water and polyols, is also often used in a cleaning composition to dissolve surfactants and active ingredients, thus allowing easier use of the product. Although it is not essential to selectively add beautifying and cleaning adjuvants, more than one beautifying and cleaning adjuvants are also added so as to achieve the usability of a cleaning composition in the field of personal care products.

Cleaning and decontamination alone are not enough for a cleaning composition, and consumers wish to buy a cleaning composition with thick appearance. Consumers think that a thick cleaning composition is a product with fine performance and higher active matter content, and therefore believe that it is safe and cost-effective. Meanwhile, a thick cleaning composition can be packaged in a hose or a similar packaging container such that the cleaning composition will not flow out like water when the hose cap is opened. A thick cleaning composition is beneficial to reducing packaging cost for manufacturers, while convenient to use and carry for consumers.

Most of the traditional thick cleaning compositions currently available on the market are those compositions with high-content fatty acid soap as a major component, such as "a stable foaming cream" with fatty acid soap as a major component described in EP1166747 filed by Oreal. But thick cleaning compositions with fatty acid soap as a major component have a higher pH value (usually the pH value is 9-11), which will cause skin allergy, redness and swelling, and hair damage to some consumers. From the perspective of safety, cleaning compositions with fatty acid soap as a major component have no substantial progress over bar soap with regard to use safety of consumers.

In the art, to produce a thick cleaning composition with a pH value in a neutral or weakly acidic range, various associating thickening components are commonly used in its formula to achieve the purpose of product thickening. Associating thickening components are mainly associating polymers, which are usually polymers with hydrophilic groups and hydrophobic groups formed by grafting a small number of hydrophobic groups such as alkyl chains and alkyl oxyethyl chains to water-soluble polymers. Hydrophobic groups in surfactants and hydrophobic groups in associating polymers associate with each other in the presence of the surfactants due to mutual association of the hydrophobic groups, and then the surfactants form micelles (like strings of small water droplets on a cobweb) on or near chains of the associating polymers, thus increasing the viscosity of the cleaning composition due to this association. Such associating polymers, such as a hydrophilic amphoteric polymer described in WO00/39176 filed by Bfgoodrich Co., are used as components in personal care products to achieve the purpose of thickening and rheology modification.

Cleaning compositions using associating polymer components have very obvious disadvantages as follows: thick cleaning compositions will often be adhered to skin and hair surfaces during use such that they are difficult to be spread out, and the cleaning compositions will have large viscosity change due to the influence of temperature change, thus they look like fruit jelly in winter but are as thin as water in summer. In particular, the cleaning compositions are not easy to be spread out when used in winter, thus affecting foaming speed and foaming effect thereof. For cleaning compositions, foaming speed and foaming effect belong to another important factor for consumers to evaluate product quality. Accordingly, consumers are not satisfied with and can not accept the cleaning compositions using associating thickening components.

SUMMARY OF THE INVENTION

Through extensive and in-depth study, the inventors have surprisingly found that surfactant lyotropic liquid crystal phase is induced to be formed when long-chain fatty acyl acidic amino acid esters and fatty compounds are used together. Since stable liquid crystal phase is formed in a cleaning composition, the amount of surfactants to be used can be reduced, and the cleaning composition is advantageously characterized by high consistency, good thixotropy, rapid foaming and good foam quality. The inventors complete the invention on the above basis.

Composition

The inventor provides a thick cleaning composition, comprising the following components (a), (b), (c) and (d) based on weight percentage:

a component (a): one or more long-chain fatty acyl acidic amino acid esters, which accounts for 0.01%-30% of the cleaning composition based on weight percentage;

a component (b): one or more fatty compounds selected from fatty acids, fatty alcohols, fatty alcohol ethers or polyol fatty acid esters, which accounts for 0.1%-50% of the cleaning composition based on weight percentage;

a component (c): one or more surfactants, which accounts for 1%-80% of the cleaning composition based on weight percentage; and a component (d): a solvent composed of one or more substances selected from water, lower alcohols, polyols and polyol ethers, which accounts for 10%-90% of the cleaning composition based on weight percentage.

Although claims of the invention particularly indicate and clearly claim the protection scope of "a thick cleaning composition" of the invention, it is to be believed that the invention will be better understood in light of the following description.

The thick cleaning composition provided by the invention is a surfactant lyotropic liquid crystal composition which at least comprises a lamellar phase liquid crystal or (and) a hexagonal phase liquid crystal or (and) a cubic phase liquid crystal.

The thick (or highly viscous) rheological morphology and performance of all surfactant solutions are very dependent on the microstructures of the surfactant solutions, i.e. the type and size of the micelles formed by self-aggregation of the surfactants in the solutions as well as the type of the liquid crystal phase formed. It is well known that the viscosity of a surfactant solution increases linearly with the increase of the surfactant concentration, and spherical micelles and rod-shaped micelles are successively formed. Since the movement of longer micelles is limited, a solution of rod-shaped micelles is more thick.

Liquid crystal phase with long-range order and short-range disorder, such as a lamellar phase liquid crystal, a hexagonal phase liquid crystal and a cubic phase liquid crystal, can be formed by further increasing the concentration of a surfactant in a solution. Description of a "liquid crystal phase" is familiar to those skilled in the art. A "lyotropic liquid crystal" (LCC) is usually a binary or multi-component system formed by a certain concentration of a surfactant in a solvent, which is characterized by both liquid flowability and solid anisotropy. A lamellar phase liquid crystal is a lamellarly arranged structure formed by lamellar micelles of a surfactant as well as a solvent or water. A hexagonal phase liquid crystal is a hexagonal structure formed by rod-shaped micelles arranged in parallel with each other. A cubic liquid crystal is a face-centered cubic or body-centered cubic or simple cubic structure formed by cubically-packed spherical or rod-shaped micelles in a solution. Especially, the hexagonal liquid crystal and the cubic liquid crystal both have much greater viscosity than the surfactant aggregates in the solution in a micellar state.

According to some literature, the formation of a lyotropic liquid crystal from a surfactant is completely determined by the high concentration of the surfactant in a solution and strongly affected by temperature. Brownian motion of the surfactant aggregates is quickened due to temperature rise or temperature change, thus damaging stability of the liquid crystal phase. Generally, for the lyotropic liquid crystal of a surfactant, the liquid crystal phase structure can only be kept stable within a narrow temperature range.

Through extensive and in-depth study, the inventors have surprisingly found that the use of long-chain fatty acyl acidic amino acid esters and fatty compounds together can advantageously induce a surfactant solution to form a stable liquid crystal phase within a wider temperature range and can reduce the amount of the surfactant to be used. Thixotropy and foam quality of the cleaning composition are also improved due to the stable existence of the liquid crystal phase.

There are many methods for identifying the liquid crystal phase of a surfactant solution. For example, an optical polarizing microscope can be used to observe the characteristic optical texture of the liquid crystal. Differential scanning calorimetry can be used to determine the temperature range for the existence of the liquid crystal and the phase-transition temperature by judging whether phase transition occurs. Small angle X-ray scattering can be used to accurately determine the structure of the liquid crystal phase, wherein the structural characteristics of the liquid crystal determine that each liquid crystal has its own characteristic interplanar spacing ratio, and thus the calculation results of Bragg Equation can be used to judge the existence and type of a liquid crystal. $^2$H-NMR (nuclear magnetic resonance) can be used to judge the type of a liquid crystal based on the splitting amplitudes of pairs of split peaks resulting from quadrupole splitting of the quadrupole moment of $^2$H nucleus in non-homogeneous environment. Freeze fracture electron microscopy can be used to observe the fracture surface of the liquid crystal through an electron microscope so as to determine the structure type of the liquid crystal, wherein the fracture surface is reproduced by platinum-carbon metal deposition.

At present, it is generally accepted that small angle X-ray scattering is the most effective and direct method for determining the existence of a liquid crystal phase and the type of the liquid crystal.

In the thick cleaning composition provided by the invention, the component (a), one or more long-chain fatty acyl acidic amino acid esters, has the following structural characteristics in the structure thereof:

I) an amino acid moiety is derived from acidic amino acids with the number of amino groups less than that of carboxyl groups, i.e. acidic amino acids with 3-8 carbon atoms that have 1 amino group and 2 carboxyl groups in an amino acid structure, including D-type, L-type and DL-type optical isomers thereof.

Specific examples of these acidic amino acids include: aminomalonic acid, aspartic acid, glutamic acid, α-aminoadipic acid, β-aminoadipic acid, α-aminopimelic acid, β-aminopimelic acid, γ-aminopimelic acid, α-aminosuberic acid, β-aminosuberic acid, γ-aminosuberic acid, α-amino-α-methylsuccinic acid, γ-methylglutamic acid, γ-methyleneglutamic acid, etc.

II) a long-chain fatty acyl moiety is linear or branched, saturated or unsaturated fatty acid-derived acyl with 8-22 carbon atoms.

Specific examples of the fatty acid-derived acyl include: acyl of linear saturated fatty acids such as octanoic acid, nonanoic acid, decanoic acid, undecanoic acid, lauric acid, tridecanoic acid, myristic acid, pentadecylic acid, palmitic acid, heptadecanoic acid, steric acid, nonadecanoic acid, arachidic acid, heneicosioc acid and docosanoic acid, branched saturated fatty acids such as butyl-5-methylpentanoic acid, 2-isobutyl-5-methylpentanoic acid, dimethyloctanoic acid, dimethylnonanoic acid, 2-butyl-5-methylhexanoic acid, methylhendecoic acid, dimethyldecanoic acid, 2-ethyl-3-methylnonanoic acid, 2,2-dimethyl-4-ethyloctanoic acid, methyldodecanic acid, 2-propyl-3-methylnonanoic acid, methyltridecanoic acid, dimethyldodecanic acid, 2-butyl-3-methylnonanoic acid, methyltetradecanoic acid, ethyltridecanoic acid, propyldodecanic acid, butylundecanoic acid, pentyldecanoic acid, hexylnonanoic acid, 2-(3-methylbutyl)-3-methylnonanoic acid, 2-(2-methylbutyl)-3-methylnonanoic acid, butylethylnonanoic acid, methylpentadecylic acid, ethyltetradecanoic acid, propyltridecanoic acid, butyldodecanic acid, pentylundecanoic acid, hexyldecanoic acid, heptylnonanoic acid, dimethyltetradecanoic acid, butylpentylheptanoic acid, trimethyltridecanoic acid, methylhexadecanoic acid, ethylpentadecylic acid, propyltetradecanoic acid, butyltridecanoic acid, pentyldodecanic acid, hexylundecanoic acid, heptyldecanoic acid, methylheptylnonanoic acid, dipentylheptanoic acid, methylheptadecanoic acid, ethylhexadecanoic acid, propylpentadecylic acid, butyltetradecanoic acid, pentyltridecanoic acid, hexyldodecanic acid, heptylundecanoic acid, octyldecanoic acid, dimethylhexadecanoic acid, methyloctylnonanoic acid, methyloctadecanoic acid, ethylheptadecanoic acid, dimethylheptadecanoic acid, methyloctyldecanoic acid, methylnonadecanoic acid, dimethyloctadecanoic acid, butylheptylnonanoic acid, methylarachidic acid, dimethylnonadecanoic acid, nonyllauric acid, dimethylarachidic acid and hexylhexadecanoic acid, linear monoenoic acids such as octenoic acid, nonenoic acid, caproleic acid, undecylenic acid, lauroleic acid, tridecylenic acid, myristoleic acid, pentadecylenic acid, hexadecenoic acid, heptadecenoic acid, octadecenoic acid, oleic acid and nonadecyenoic acid, branched monoenoic acids such as methylheptenoic acid, methylnonenoic acid, methylundecylenic acid dimethylcaproleic acid, methyldodecenoic acid, methyltridecylenic acid, dimethyldodecenoic acid, dimethyltridecylenic acid, methyloctadecenoic acid, dimethylheptadecenoic acid and ethyloctadecenoic acid, and polyenoic acids such as linoleic acid, linolelaidic acid, linolenic acid, 9,12,15-octadecatrienoic acid, 10,12,14-octadecatrienoic acid, parinaric acid and arachidonic acid; the fatty acid-derived acyl can also include acyl of natural fatty acids such as coconut oil fatty acid, palm oil fatty acid, palm kernel oil fatty acid, corn oil fatty acid, peanut oil fatty acid, cottonseed oil fatty acid, linseed oil fatty acid, sunflower seed oil fatty acid, soybean oil fatty acid, sesame oil fatty acid, castor seed oil fatty acid, olive oil fatty acid, tea-seed oil fatty acid, tallow fatty acid, hydrogenated tallow fatty acid, lard fatty acid and fish oil fatty acid, as well as acyl of a mixture of the above various fatty acids; and the fatty acid-derived acyl is preferably acyl derived from linear fatty acids with 12-22 carbon atoms, such as caprylic acid, capric acid, lauric acid, myristic acid, palmitic acid, stearic acid, arachidic acid and docosanoic acid.

) an ester group moiety is monoester, diester or a mixture thereof formed by 2 carboxyl groups of amino acid and saturated or unsaturated, linear or branched fatty alcohols with 8-28 carbon atoms or (and) fatty alcohol ethers thereof with polyoxyalkylene having addition mole number of 1-30.

Specific examples of these linear or branched fatty alcohols forming esters include: fatty alcohols such as octyl alcohol, 2-ethylhexanol, sec-octyl alcohol, isooctyl alcohol, nonanol, sec-nonanol, decanol, iso-decanol, sec-decanol, undecanol, sec-undecanol, 2-methyldecanol, lauryl alcohol, sec-dodecyl alcohol, tridecanol, isotridecanol, myristyl alcohol, sec-tetradecyl alcohol, pentadecyl alcohol, sec-pentadecyl alcohol, cetyl alcohol, palmityl alcohol, sec-hexadecanol, heptadecanol, sec-heptadecanol, stearyl alcohol, isostearyl alcohol, sec-octadecanol, oleyl alcohol, eicosanol, docosyl alcohol, tetracosanol, hexacosanol, octacosanol, 2-butylhexanol, 2-butyldecanol, 2-hexyloctyl alcohol, 2-hexyldecanol, 2-hexyldodecyl alcohol, 2-octyldecanol, 2-octyldodecyl alcohol, 2-octyltetradecyl alcohol, 2-decyldodecyl alcohol, 2-decyltetradecyl alcohol, 2-decylhexadecanol, 2-dodecyltetradecyl alcohol and 2-dodecylhexadecanol, as well as a mixture thereof.

Preferably, the acidic amino acid moiety in the structures of the long-chain fatty acyl acidic amino acid esters is derived from aspartic acid and glutamic acid.

Preferably, the long-chain fatty acyl acidic amino acid esters have acyl of linear saturated fatty acids with 12-18 carbon atoms in the structures thereof.

Preferably, the long-chain fatty acyl acidic amino acid esters have monoester, diester or a mixture thereof formed by linear or branched saturated fatty alcohols with 12-22 carbon atoms in the structures thereof.

The long-chain fatty acyl acidic amino acid esters are selected from one or more of the following esters: N-lauroyl L-aspartic acid cetyl ester, N-lauroyl L-aspartic acid stearyl ester, N-lauroyl L-aspartic acid docosyl ester, N-lauroyl L-glutamic acid cetyl ester, N-lauroyl L-glutamic acid stearyl ester, N-lauroyl L-glutamic acid docosyl ester, N-lauroyl L-glutamic acid isododecyl ester, N-lauroyl L-glutamic acid isotridecyl ester, N-lauroyl L-glutamic acid hexyldecyl ester, N-lauroyl L-glutamic acid isostearyl ester, N-lauroyl L-glutamic acid octyldodecyl ester, N-lauroyl L-aspartic acid isododecyl ester, N-lauroyl L-aspartic acid isotridecyl ester, N-lauroyl L-aspartic acid hexyldecyl ester, N-lauroyl L-aspartic acid isostearyl ester, N-lauroyl L-aspartic acid octyldodecyl ester, N-myristoyl L-aspartic acid cetyl ester, N-myristoyl L-aspartic acid stearyl ester, N-myristoyl L-aspartic acid docosyl ester, N-myristoyl L-glutamic acid cetyl ester, N-myristoyl L-glutamic acid stearyl ester, N-myristoyl L-glutamic acid docosyl ester, N-myristoyl L-glutamic acid isododecyl ester, N-myristoyl L-glutamic acid isotridecyl ester, N-myristoyl L-glutamic acid hexyldecyl ester, N-myristoyl L-glutamic acid isostearyl ester, N-myristoyl L-glutamic acid octyldodecyl ester, N-myristoyl L-aspartic acid isododecyl ester, N-myristoyl L-aspartic acid isotridecyl ester, N-myristoyl L-aspartic acid hexyldecyl ester, N-myristoyl L-aspartic acid isostearyl ester, N-myristoyl L-aspartic acid octyldodecyl ester, N-palmitoyl L-aspartic acid isododecyl ester, N-palmitoyl L-aspartic acid isotridecyl ester, N-palmitoyl L-aspartic acid hexyldecyl ester, N-palmitoyl L-aspartic acid isostearyl ester, N-palmitoyl L-aspartic acid octyldodecyl ester, N-palmitoyl L-aspartic acid cetyl ester, N-palmitoyl L-aspartic acid stearyl ester, N-palmitoyl L-aspartic acid docosyl ester, N-palmitoyl L-glutamic acid cetyl ester, N-palmitoyl L-glutamic acid stearyl ester, N-palmitoyl L-glutamic acid docosyl ester, N-palmitoyl L-glutamic acid isododecyl ester, N-palmitoyl L-glutamic acid isotridecyl ester, N-palmitoyl L-glutamic acid hexyldecyl ester, N-palmitoyl L-glutamic acid isostearyl ester, N-palmitoyl glutamic acid L-octyldodecyl ester, N-stearoyl L-aspartic acid cetyl ester, N-stearoyl L-aspartic acid stearyl ester, N-stearoyl L-aspartic acid docosyl ester, N-stearoyl L-glutamic acid cetyl ester, N-stearoyl L-glutamic acid stearyl ester, N-stearoyl L-glutamic acid docosyl ester, N-stearoyl L-glutamic acid isododecyl ester, N-stearoyl L-glutamic acid isotridecyl ester, N-stearoyl L-glutamic acid hexyldecyl ester, N-stearoyl L-glutamic acid isostearyl ester, N-stearoyl L-glutamic acid octyldodecyl ester, N-stearoyl aspartic acid isododecyl ester, N-stearoyl aspartic acid isotridecyl ester, N-stearoyl aspartic acid hexyldecyl ester, N-stearoyl aspartic acid isostearyl ester and N-stearoyl aspartic acid octyldodecyl ester.

Preferably, the long-chain fatty acyl acidic amino acid esters are selected from one or more than one of the following esters: N-lauroyl L-aspartic acid cetyl ester, N-lauroyl L-aspartic acid stearyl ester, N-lauroyl L-aspartic acid docosyl ester, N-lauroyl L-glutamic acid cetyl ester, N-lauroyl L-glutamic acid stearyl ester, N-lauroyl L-glutamic acid docosyl ester, N-lauroyl glutamic acid isotridecyl ester, N-lauroyl L-glutamic acid isostearyl ester, N-lauroyl L-aspartic acid isotridecyl ester, N-lauroyl L-aspartic acid isostearyl ester, N-myristoyl L-aspartic acid cetyl ester, N-myristoyl L-aspartic acid stearyl ester, N-myristoyl L-aspartic acid docosyl ester, N-myristoyl L-glutamic acid cetyl ester, N-myristoyl L-glutamic acid stearyl ester, N-myristoyl L-glutamic acid docosyl ester, N-myristoyl glutamic acid isotridecyl ester, N-myristoyl L-glutamic acid isostearyl ester, N-myristoyl glutamic acid octyldodecyl ester, N-myristoyl L-aspartic acid isotridecyl ester, N-myristoyl L-aspartic acid isostearyl ester, N-palmitoyl L-aspartic acid isotridecyl ester, N-palmitoyl L-aspartic acid isostearyl ester, N-palmitoyl L-aspartic acid cetyl ester, N-palmitoyl L-aspartic acid stearyl ester, N-palmitoyl L-aspartic acid docosyl ester, N-palmitoyl L-glutamic acid cetyl ester, N-palmitoyl L-glutamic acid stearyl ester, N-palmitoyl L-glutamic acid docosyl ester, N-palmitoyl L-glutamic acid isotridecyl ester, N-palmitoyl L-glutamic acid hexyldecyl ester, N-palmitoyl L-glutamic acid isostearyl ester, N-stearoyl L-aspartic acid cetyl ester, N-stearoyl L-aspartic acid stearyl ester, N-stearoyl L-aspartic acid docosyl ester, N-stearoyl L-glutamic acid cetyl ester, N-stearoyl L-glutamic acid stearyl ester, N-stearoyl L-glutamic acid docosyl ester, N-stearoyl L-glutamic acid isotridecyl ester, N-stearoyl L-glutamic acid isostearyl ester, N-stearoyl L-aspartic acid isotridecyl ester and N-stearoyl aspartic acid isostearyl ester.

More preferably, the long-chain fatty acyl acidic amino acid esters are selected from one or more of the following esters: N-lauroyl L-aspartic acid docosyl ester, N-lauroyl L-glutamic acid cetyl ester, N-lauroyl glutamic acid isotridecyl ester, N-lauroyl L-glutamic acid isostearyl ester, N-lauroyl L-aspartic acid isotridecyl ester, N-lauroyl L-aspartic acid isostearyl ester, N-myristoyl L-aspartic acid stearyl ester, N-myristoyl L-glutamic acid cetyl ester, N-myristoyl glutamic acid isotridecyl ester, N-myristoyl L-glutamic acid isostearyl ester, N-myristoyl L-aspartic acid isotridecyl ester, N-myristoyl L-aspartic acid isostearyl ester, N-palmitoyl L-aspartic acid isotridecyl ester, N-palmitoyl L-aspartic acid isostearyl ester, N-palmitoyl L-glutamic acid stearyl ester, N-palmitoyl L-glutamic acid isotridecyl ester, N-palmitoyl L-glutamic acid hexyldecyl ester, N-palmitoyl L-glutamic acid isostearyl ester, N-stearoyl L-aspartic acid cetyl ester, N-stearoyl L-aspartic acid stearyl ester, N-stearoyl L-glutamic acid stearyl ester, N-stearoyl L-glutamic acid docosyl ester, N-stearoyl L-glutamic acid isotridecyl ester and N-stearoyl L-glutamic acid isostearyl ester.

In the invention, the component (a), the long-chain fatty acyl acidic amino acid ester(s), preferably accounts for 0.1-20% of the cleaning composition based on weight percentage, more preferably 0.2-10% and most preferably 0.5-3%.

In the thick cleaning composition provided by the invention, the component (b): one or more fatty compounds selected from fatty acids, fatty alcohols, fatty alcohol ethers or polyol fatty acid esters.

The fatty acids are linear or branched, saturated or unsaturated fatty acids with 8-22 carbon atoms.

These fatty acids are selected from one or more of the following acids: saturated fatty acids such as octanoic acid, nonanoic acid, decanoic acid, undecanoic acid, lauric acid, tridecanoic acid, myristic acid, pentadecylic acid palmitic acid, heptadecanoic acid, steric acid, nonadecanoic acid, arachidic acid, heneicosioc acid, docosanoic acid, isostearic acid, 2-butyl-5-methylpentanoic acid, 2-isobutyl-5-methylpentanoic acid, dimethyloctanoic acid, dimethylnonanoic acid, 2-butyl-5-methylhexanoic acid, methylhendecoic acid, dimethyldecanoic acid, 2-ethyl-3-methylnonanoic acid, 2,2-dimethyl-4-ethyloctanoic acid, methyldodecanoic acid, 2-propyl-3-methylnonanoic acid, methyltridecanoic acid, dimethyldodecanic acid, 2-butyl-3-methylnonanoic acid, methyltetradecanoic acid, ethyltridecanoic acid, propyldodecanoic acid, butylundecanoic acid, pentyldecanoic acid, hexylnonanoic acid, 2-(3-methylbutyl)-3-methylnonanoic acid, 2-(2-methylbutyl)-3-methylnonanoic acid, butylethylnonanoic acid, methylpentadecylic acid, ethyltetradecanoic acid, propyltridecanoic acid, butyldodecanic acid, pentyl­decanoic acid, hexyldecanoic acid, heptylnonanoic acid, dimethyltetradecanoic acid, butylpentylheptanoic acid, trimethyltridecanoic acid, methylhexadecanoic acid, ethylpentadecylic acid, propyltetradecanoic acid, butyltridecanoic acid, pentyldodecanoic acid, hexylundecanoic acid, heptyldecanoic acid, methylheptylnonanoic acid, dipentylheptanoic acid, methylheptadecanoic acid, ethylhexadecanoic acid, propylpentadecylic acid, butyltetradecanoic acid, pentyltridecanoic acid, hexyldodecanoic acid, heptylundecanoic acid, octyldecanoic acid, dimethylhexadecanoic acid, methyloctylnonanoic acid, methyloctadecanoic acid, ethylheptadecanoic acid, dimethylheptadecanoic acid, methyloctyldecanoic acid, methylnonadecanoic acid, dimethyloctadecanoic acid, butylheptylnonanoic acid, methylarachidic acid, dimethylnonadecanoic acid, nonyllauric acid, dimethylarachidic acid and hexylhexadecanoic acid, unsaturated fatty acids such as octenoic acid, nonenoic acid, caproleic acid, undecylenic acid, lauroleic acid, tridecylenic acid, myristoleic acid, pentadecylenic acid, hexadecenoic acid, heptadecenoic acid, octadecenoic acid, oleic acid, nonadecenoic acid, methylheptenoic acid, methylnonenoic acid, methylundecylenic acid, dimethylcaproleic acid, methyldodecenoic acid, methyltridecylenic acid, dimethyldodecenoic acid, dimethyltridecylenic acid, methyloctadecenoic acid, dimethylheptadecenoic acid, ethyloctadecenoic acid, linoleic acid, linolelaidic acid, linolenic acid, 9,12,15-octadecatrienoic acid, 10,12,14-octadecatrienoic acid, parinaric acid and arachidonic acid; and mixed fatty acids derived from natural grease: coconut oil fatty acid, palm oil fatty acid, palm kernel oil fatty acid, corn oil fatty acid, peanut oil fatty acid, cottonseed oil fatty acid, linseed oil fatty acid, sunflower seed oil fatty acid, soybean oil fatty acid, sesame oil fatty acid, castor seed oil fatty acid, olive oil fatty acid, tea-seed oil fatty acid, tallow fatty acid, hydrogenated tallow fatty acid, lard fatty acid, fish oil fatty acid, etc.

Preferably, the fatty acids are linear or branched saturated fatty acids with 12-22 carbon atoms.

The fatty alcohols or (and) the fatty alcohol ethers are linear or branched, saturated or unsaturated fatty alcohols with 8-28 carbon atoms, or (and) fatty alcohol ethers thereof with polyoxyalkylene having addition mole number of 1-30.

The fatty alcohols or (and) the fatty alcohol ethers are selected from one or more of the following: fatty alcohols such as octyl alcohol, 2-ethylhexanol, sec-octyl alcohol, isooctyl alcohol, nonanol, sec-nonanol, 1-decanol, isodecanol, sec-decanol, undecanol, sec-undecanol, 2-methyldecanol, lauryl alcohol, sec-dodecyl alcohol, 1-tridecanol, isotridecanol, myristyl alcohol, sec-tetradecyl alcohol, pentadecyl alcohol, sec-pentadecyl alcohol, cetyl alcohol, palmityl alcohol, sec-hexadecanol, heptadecanol, sec-heptadecanol, stearyl alcohol, isostearyl alcohol, sec-octadecanol, oleyl alcohol, docosyl alcohol, eicosanol, tetracosanol, hexacosanol, octacosanol, 2-butylhexanol, 2-butyldecanol, 2-hexyloctyl alcohol, 2-hexyldecanol, 2-hexyldodecyl alcohol, 2-octyldecanol, 2-octyldodecyl alcohol, 2-octyltetradecyl alcohol, 2-decyldodecyl alcohol, 2-decyltetradecyl alcohol, 2-decylhexadecanol, 2-dodecyltetradecyl alcohol and 2-dodecylhexadecanol; and the fatty alcohol ethers are fatty alcohol ethers of the above fatty alcohols with polyoxyalkylene having addition mole number of 1-30. Preferably, the fatty alcohols or (and) the fatty alcohol ethers are linear or branched saturated fatty alcohols with 12-22 carbon atoms, or (and) fatty alcohol ethers thereof with polyoxyalkylene having addition mole of number 1-7.

The polyol fatty acid esters are polyol fatty acid esters formed by polyols having 2-6 hydroxyl groups and linear or branched, saturated or unsaturated fatty acids having 8-22 carbon atoms.

The polyol fatty acid esters are selected from one or more of the following: glyceryl monostearate, glyceryl dilaurate, ethylene glycol monolaurate, ethylene glycol monostearate, ethylene glycol dilaurate, ethylene glycol distearate, propylene glycol monolaurate, butylene glycol monopalmitate, diglycol dilaurate, diglyceryl dilaurate, trilaurin, glyceryl monopalmitate, tripalmitin, glyceryl tristearate, caprylic-capric triglyceride, diglyceryl monolaurate, diglyceryl distearate, pentaerythritol monolaurate, pentaerythritol tetrapalmitate, pentaerythrityl tetrastearate, pentaerythritol tetraisostearate, methyl gluoside laurate, sorbitol anhydride dioleate, etc.

Preferably, the polyol fatty acid esters are polyol fatty acid esters formed by polyols having 2-6 hydroxyl groups and linear saturated fatty acids having 12-18 carbon atoms.

In the invention, the fatty compounds are preferably selected from one or more of the following: lauric acid, myristic acid, palmitic acid, stearic acid, isostearic acid, docosanoic acid, lauryl alcohol, isotridecanol, docosyl alcohol, glyceryl stearate, trilaurin and pentaerythritol tetrastearate.

In the invention, the component (b), the fatty compound(s), preferably accounts for 0.1%-35% of the cleaning composition based on weight percentage, more preferably 0.5-20%.

In the thick cleaning composition provided by the invention, the component c), the surfactant(s), is selected from anionic surfactants, zwitterionic surfactants, nonionic surfactants and cationic surfactants or a mixture thereof.

Among the surfactants, the anionic surfactants are selected from one or more of the following: carboxylate, alkyl polyoxyethylene ether carboxylate, alkyl sulfate, alkyl polyoxyethylene ether sulfate, alkylamide ether sulfate, alkylaryl polyether sulfate, alkyl sulfonate, alkyl polyoxyethylene ether sulfonate, alkylamide sulfonate, alkylaryl sulfonate, α-alkene sulfonate, petroleum sulfonate, alkyl phosphate salt, alkyl polyoxyethylene ether phosphate salt, acyl isethionate salt, fatty acyl amino acid salt, fatty acyl taurine salt, sulfosuccinate salt, acyl lactate, etc.;

Alkyl or acyl of all the above compounds can be selected from alkyl or acyl containing 8-30 carbon atoms, and aryl can be selected from phenyl or benzyl. The average addition mole number of polyoxyethylene is 2-50 mol. The above salts include alkali metal salts such as potassium salts and sodium salts; alkaline earth metal salts such as magnesium salts; ammonium salts; organic amine salts; alkanolamine salts such as diethanolamine salts, triethanolamine salts and diisopropanolamine salts; or basic amino acid salts such as lysine salts and arginine salts;

The zwitterionic surfactants are selected from one or more of the following: alkyl betaine; alkylamide betaine; sulphobetaine; sulfite and sulfate betaine; phosphinate and phosphonate betaine; phosphite and phosphate betaine; imidazoline amphoteric surfactants: amphoteric acetate and amphoteric propionate; amino acid type amphoteric surfactants: long-chain alkyl amino acid salt, N-alkyl polyamine ethyl glycinate, alkyl polyamine polyamino acid salt, etc.;

The nonionic surfactants are selected from one or more of the following: fatty glyceride polyoxyethylene ether; alkyl phenol polyoxyethylene ether; fatty acid polyoxyethylene ester; alkanolamide; polyoxyethylene alkanolamide; polyoxyethylene sorbitan fatty acid ester; polyoxyethylene fatty acid xylitol ester, alkyl glycoside, etc.; and The cationic surfactants are selected from one or more of the following: long-chain alkyl trimethyl ammonium halide; long-chain alkyl dimethyl benzyl ammonium halide; long-chain amide alkyl dimethyl benzyl ammonium halide; di(long-chain amide alkyl)dibenzyl ammonium halide; imidazoline quaternary ammonium salt; alkyl pyridinium salt, etc.

Preferably, the surfactants are anionic surfactants.

In the invention, the component (c), the surfactant(s), preferably accounts for 5-50% of the cleaning composition based on weight percentage, more preferably 10-40%, and most preferably 15-25%.

In the thick cleaning composition provided by the invention, the component d) is selected from water, lower alcohol, polyol and polyol ether; and the component d) is selected from one or more of the following: pure water, distilled water, deionized water, mineral water, ethanol, propanol, isopropanol, ethylene glycol, polyethylene glycol with different molecular weight, diethylene glycol, propylene glycol, polypropylene glycol with different molecular weight, dipropylene glycol, glycerol, polyglycerol, maltitol, sorbierite, etc.

In the invention, the solvent preferably accounts for 35-80% of the cleaning composition based on weight percentage, more preferably 55-80%.

During preparation of the cleaning composition, various traditional beautifying or cleaning adjuvants can be added without affecting stability according to the end use.

The thick cleaning composition provided by the invention can also comprise one or more beautifying and cleaning adjuvants for skin, eyes, teeth and hair, i.e. rheology modifiers, humectants, polymers, superfatting agents, saccharides, powders, siloxane, pearlescing agents, pH regulators, opacifiers, special ingredients of cosmetics and therapeutic cosmetics, preservatives, chelating agents, antimicrobial agents, antioxidants, dye or essence.

Various traditional beautifying and cleaning adjuvants are only auxiliary materials of the invention, but for further understanding and describing the examples, these additives are exemplified as follows:

The rheology modifiers: hydrophobically modified associating polymers, hydrophobically modified non-ionic polyols, cellulose derivatives, etc. The rheology modifiers which are used in a small amount for the purpose of thickening are especially beneficial for further realizing the object of the invention. For example, the rheology modifiers include PEG-120 methyl glucoside dioleate, PEG-150 pentaerythritol tetrastearate, PEG-75 dioleate and PEG-150 distearate.

The humectants: sodium chondroitin sulfate, sodium hyaluronate, sodium adenosine phosphate, sodium lactate, pyrrolidone carboxylate, etc.;

The polymers: polyvinylpyrrolidone, etc.;

The superfatting agents: animal and vegetable fat derivatives, fatty acid esters, etc.;

The saccharides: maltose, glucose, fructose, etc.;

The powders: modified or unmodified silicon dioxide, bentonite, diatomite, modified starch, lauroyl lysine, etc.;

The siloxane: dimethyl siloxane, etc.;

The pearlescing agents: ethylene glycol monostearate, ethylene glycol distearate, etc.;

The pH regulators: citric acid, fruit acid, potassium hydroxide, sodium hydroxide, triethanolamine, etc.;

Special ingredients of cosmetics and therapeutic cosmetics: vitamins, various plant extracts, etc.;

The opacifiers: styrene/acrylate copolymers, etc.;

The preservatives: phenoxyethyl alcohol, methyl p-hydroxybenzoate, etc.;

The chelating agents: disodiumedetate, etc.;

The antimicrobial agents: zinc pyrithione, chloroxylenol, etc.; and

The antioxidants: butylated hydroxytoluene, etc.

Detailed notes of these traditional beautifying or cleaning adjuvants can be seen in *Cosmetics, Science and Technology* by Sagarin, etc. The variety and number of various traditional beautifying or cleaning adjuvants that can be used in the cleaning composition are too numerous to be exemplified one by one, and all the adjuvants can be added so long as they would not affect the stability of the cleaning composition.

The functions and functional mechanism of various components of the cleaning composition of the invention are as follows:

Surfactants and solvents play the role of cleaning and decontamination in the cleaning composition.

The function of the long-chain fatty acyl acidic amino acid esters and the fatty compounds in the cleaning composition is to induce "micelles" formed by the surfactants and the solvents to transform towards the required "liquid crystal phase" (stable liquid crystal phase can not be formed by using the fatty compounds alone), thus the cleaning composition becomes a "toothpaste-like" thick cleaning composition with "good rheological property".

The above "good rheological property" means that fluid has thick apparent viscosity and good thixotropy, wherein thixotropy refers to easy daubing and quick foaming during use of the cleaning composition.

The above term "toothpaste-like" means that viscosity is more than 10,000 cps (centipoise).

Preparation Method

The production process of the invention is a method commonly used by those skilled in the art, which is briefly described as follows: in a container equipped with stirring paddles (the stirring paddles can be anchor-type, frame-type, spiral push-type, etc.) as well as a jacket or metal coil heating and cooling system, a solvent (usually a mixed solvent of water, polyols, etc.) is first added, heating is started, the container is slowly heated to about 60° C., then other various components are sequentially added (except volatile components, preservatives and essence), the container is slowly heated to about 80° C. during stirring, and stirring is started and the temperature is kept at about 80° C. for 3 hours. After full stirring is confirmed and relevant indexes are met, a cooling system is started for cooling to about 40° C., and then volatile components, preservatives and essence are added and fully mixed before the body is discharged.

The component b), the fatty compounds, can also be pre-added to any one of the surfactants, solvents, beautifying and cleaning adjuvants, and stirred and mixed.

Key performance indicators of the cleaning composition of the invention include viscosity, foamability, pH, etc. of the cleaning composition.

Viscosity:

Viscosity of the cleaning composition of the invention is more than 10,000 cps.

Viscosity test is performed by DV-II+Pro Rotor Viscometer of Brookfield Company (TC rotor, 10 rmp), and measurement is performed at three temperature points 5/25/45.

Evaluation of Foamability:

Ten trained volunteers use cleaning compositions to perform washing test, wherein each volunteer first wets both hands with clean water, places 2 g of a cleaning composition on the left palm and adds a proper amount of water to the palm, rubbing for 30 seconds according to their usual washing habits, and gives assessment according the following grade standard.

5 scores: very easy to foam by rubbing.
4 scores: easy to foam by rubbing.
3 scores: ordinary foaming speed by rubbing.
2 scores: relatively difficult to foam by rubbing.
1 score: very difficult to foam by rubbing.

The assessed scores are added together, and each composition is graded according to the following standard.

Grade A: 45 scores
Grade B: 35-44 scores
Grade C: 25-35 scores
Grade D: below 25 scores pH Test:

A Mettler pH tester is used to test pH value of 10% aqueous solution of the cleaning composition.

Stability Evaluation:

The cleaning compositions of the invention are respectively placed in 60° C. and 45° C. ovens as well as 5° C. and −15° C. refrigerators for 6 months, and then the body state is visually observed and the viscosity at various temperature points is retested.

Differential scanning calorimetry (DSC) is used to judge temperature range and phase-transition temperature of liquid crystal phase.

Identification of Liquid Crystals:

Small angle X-ray scattering (SAXS) technology is used to identify liquid crystals.

The small angle X-ray scattering technology can be used to accurately judge the specific liquid crystal morphology of lyotropic liquid crystals. The lyotropic liquid crystals are periodic structures with long-range order formed after oriented arrangement of amphiphilic molecules in solvents. Since electron cloud densities of solvents and amphiphilic molecules are different, the small angle X-ray scattering technology can be used to determine the structure of liquid crystal phase and calculate lattice parameters. According to Bragg Equation $2d \sin \theta = n\lambda$, interplanar spacings of liquid crystal phases with different morphologies have different proportional relations, scattering vectors corresponding to various levels of Bragg peaks on the SAXS curves have different proportions, and the specific morphology of liquid crystal phase of lyotropic liquid crystals can be distinguished based on different proportions.

Use

The thick cleaning composition provided by the invention is used for the purpose of cleaning skin, eyes, teeth and hair. Specifically, the examples include facial cleansers, facial washes, paste shampoos, hair conditioners, toothpastes, etc.

The invention further provides a new use of the long-chain fatty acyl acidic amino acid esters for inducing formation of liquid crystals, especially for inducing formation of surfactant lyotropic liquid crystals, preferably formation of at least one of the following liquid crystals: the lamellar liquid crystal, the hexagonal liquid crystal or the cubic liquid crystal.

The above features mentioned in the invention or features mentioned in the examples can be combined in any way.

The main advantages of the invention are as follows:

After adopting the above technical measures, the invention has the following benefits: the thick cleaning composition can achieve satisfactory thick appearance when used for cleaning skin and hair, can maintain relatively stable viscosity at different temperature conditions, and is easily daubed and quickly foamed with good foaming quality when used by consumers. The cleaning composition can form thick and stable appearance at a wide range of pH conditions, and is especially suitable for formulating cleaning compositions with low irritability and high safety which have neutral and weakly acidic pH.

BRIEF DESCRIPTION OF THE DRAWINGS

Small angle X-ray scattering results herein are determined by SAXsess X-ray Scatterometer manufactured by PANalytical B.V., Holland.

FIG. 1 shows that after determination by the small angle X-ray scattering, the ratio of the scattering vectors corresponding to levels 1, 2 and 3 scattering peaks q1:q2:q3 is equivalent to 1:2:3 in the composition provided by Example 4 of the invention. This shows that the cleaning composition is a liquid crystal structure with lamellar phase.

FIG. 2 shows that after determination by the small angle X-ray scattering, the ratio of the scattering vectors corresponding to levels 1, 2 and 3 scattering peaks q1:q2:q3 is equivalent to $1:\sqrt{2}, \sqrt{4}$ in the composition provided by Example 20 of the invention. This shows that the cleaning composition is a liquid crystal structure with hexagonal phase.

DETAILED DESCRIPTION OF THE INVENTION

Figure 1:
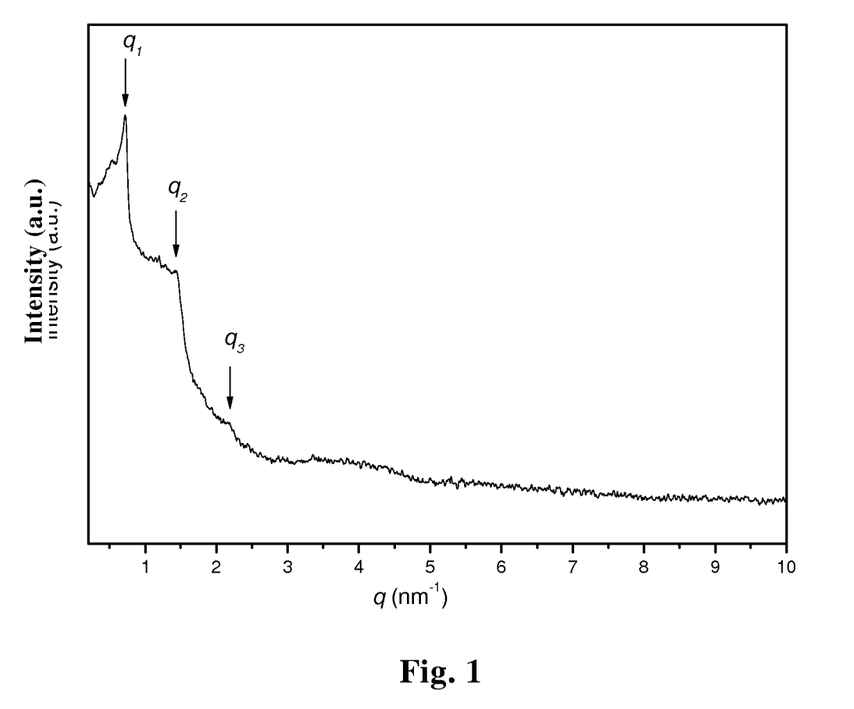
FIG. 1 shows the results determined by small angle X-ray scattering for the cleaning composition provided by Example 4 of the invention. In the figure, X axis represents scattering vector q corresponding to scattering peaks, and Y axis represents the intensity of the scattering peaks.
Figure 2:
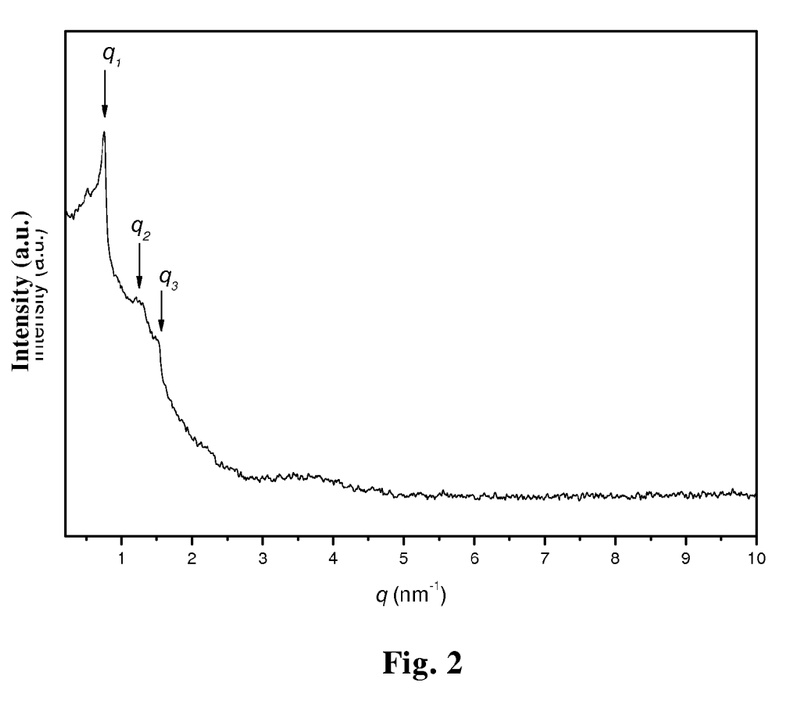
FIG. 2 shows the results determined by the small angle X-ray scattering for the composition provided by Example 20 of the invention. In the figure, X axis represents scattering vector q corresponding to scattering peaks, and Y axis represents the intensity of the scattering peaks.
Figure 3:
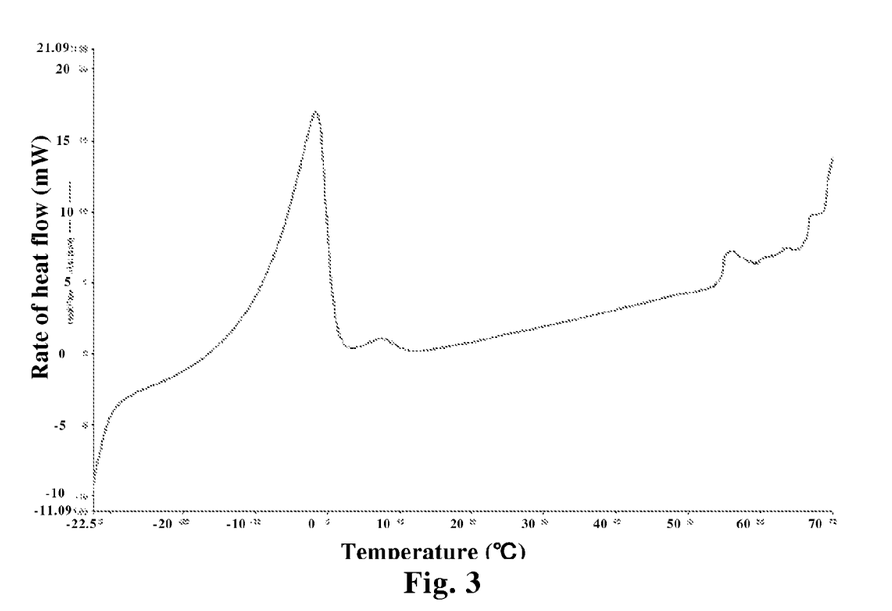
FIG. 3 shows the differential scanning calorimetry results of the composition provided by Example 20 of the invention, and the DSC thermogram is obtained by measurement with DSC8000 Differential Scanning Colorimeter from PerkinElmer, USA. In the thermogram, X axis represents temperature, and Y axis represents rate of heat flow. It can be seen from the DSC thermogram that the liquid crystal phase of the thick cleaning composition obtained according to Example 20 of the invention stably exists at the temperature ranging from about 2° C. to 55° C.

The invention will be further described below in conjunction with the specific examples. It should be understood that these examples are only used for describing the invention, rather than limiting the scope of the invention. In the following examples, the experimental methods with no specific conditions indicated are implemented according to normal conditions or conditions suggested by manufacturers.

Unless otherwise indicated, various components are given by chemical names, or names of INCI (International Nomenclature of Cosmetic Ingredients) well-known in the art.

In the examples and comparative examples, the number of a component refers to weight percentage of the corresponding component in the example. See Table 1.

The unit of weight-to-volume percentage (w/v %) in the invention is well known by those skilled in the art. For example, it refers to the weight of a solute in 100 ml solution.

Unless otherwise defined, all the professional and scientific terms used herein have the same meanings well-known by those skilled in the art. In addition, any method and material that is similar or equivalent to the recorded content can be used in the method of the invention. The preferred implementation methods and materials as described herein are only used for demonstration.

Examples 1-20

TABLE 1

| Description | Chemical names of components | Comparative Example 1 | Example 1 | Example 2 | Example 3 |
|---|---|---|---|---|---|
| Component a) | N-lauroyl L-aspartic acid cetyl ester | / | 1.5% | 8% | / |
| Component a) | N-lauroyl L-aspartic acid stearyl ester | / | 2.5% | / | / |
| Component a) | N-lauroyl L-aspartic acid docosyl ester | / | / | / | 8% |
| Component a) | N-lauroyl L-glutamic acid cetyl ester | / | / | 2% | / |
| Component b) | Lauric acid | / | 2% | 1% | 1% |
| Component b) | Myristic acid | / | 3% | / | / |
| Component b) | Palmitic acid | / | / | 1% | 1% |
| Component b) | Glyceryl stearate (monoester content of more than 90%) | / | 7% | 1.5% | 1.5% |
| Component c) | Sodium polyoxyethylene 2EO lauryl ether sulfate | 25% | 25% | 25% | 25% |
| Component c) | Sodium cocoyl sarcosinate | 2% | 2% | 2% | 2% |
| Component c) | Coco amidopropyl betaine | 5% | 5% | 5% | 5% |
| Component c) | Cocodiethanolamide | 3% | 3% | 3% | 3% |
| Component d) | Propanetriol | 15% | 15% | 15% | 15% |
| Auxiliary materials | Preservative and essence | Proper amount | Proper amount | Proper amount | Proper amount |
| Component d) | Water | Balance | Balance | Balance | Balance |
| Viscosity at 5° C. (centipoise) | | 16300 | 34500 | 51040 | 47400 |
| Viscosity at 25° C. (centipoise) | | 2750 | 32020 | 45080 | 41200 |
| Viscosity at 45° C. (centipoise) | | 1200 | 30160 | 42200 | 38100 |
| Evaluation of foamability | | A | A | A | A |
| pH value | | 6.7 | 7.0 | 6.8 | 7.1 |

In Table 1, the components a) and b) of the invention are not added in Comparative Example 1. In spite of good foaming, the viscosity is very low at normal temperature and high temperature. According to Examples 1-3 of the invention, since the components (a), (b), (c) and (d) of the invention are used, the cleaning composition not only exhibits higher viscosity, but also has relatively stable viscosity within the temperature range of 5° C.-45° C. without affecting foaming property.

Note: EO number indicated in the components is the addition mole number of polyoxyalkylene.

TABLE 2

| Description | Chemical names of components | Comparative Example 2 | Example 4 | Example 5 | Example 6 |
| --- | --- | --- | --- | --- | --- |
| Component a) | N-lauroyl L-glutamic acid stearyl ester | / | 2 | 5 | 1 |
| Component a) | N-lauroyl L-glutamic acid docosyl ester | / | 3 | / | / |
| Component a) | N-myristoyl L-aspartic acid cetyl ester | / | / | 2 | / |
| Component a) | N-myristoyl L-aspartic acid stearyl ester | / | / | 3 | / |
| Component b) | Lauric acid | / | 5 | / | 5 |
| Component b) | Glyceryl stearate (monoester content of more than 70%) | / | 2 | / | 5 |
| Component b) | Mixture of palmitic acid and stearic acid | / | / | 0.5 | 10 |
| Component b) | Docosanoic acid | / | 3 | / | / |
| Component c) | Potassium monolauryl phosphate | 32 | 32 | 32 | 32 |
| Component c) | Coco amphoteric imidazoline | 5 | 5 | 5 | 5 |
| Component c) | Cocodiethanolamide | 3 | 3 | 3 | 3 |
| Auxiliary material | PEG150 distearate | 3 | 0.2 | / | / |
| Component d) | Propylene glycol | 15 | 15 | 15 | 15 |
| Auxiliary materials | Preservative and essence | Proper amount | Proper amount | Proper amount | Proper amount |
| Component d) | Water | Balance | Balance | Balance | Balance |
| Viscosity at 5° C. (centipoise) | | 65220 | 49020 | 42460 | 36880 |
| Viscosity at 25° C. (centipoise) | | 27500 | 44120 | 38100 | 33100 |
| Viscosity at 45° C. (centipoise) | | 8240 | 39200 | 32080 | 29600 |
| Evaluation of foamability | | D | B | A | A |
| pH value | | 6.8 | 6.9 | 6.6 | 7.2 |

In Table 2, after a thickening component PEG150 distearate is added in Comparative Example 2, although the viscosity of the cleaning composition is improved, the viscosity of the cleaning composition varies greatly due to temperature effect. Thus, the product has very poor foamability. According to Example 4 of the invention, after a small amount of a thickener PEG150 distearate is added, product viscosity is further improved due to synergism, but foaming property is still somewhat affected. According to Examples 4-6 of the invention, after the components (a), (b), (c) and (d) of the invention are used in the cleaning composition, the cleaning composition not only exhibits higher viscosity, but also has relatively stable viscosity within the temperature range of 5° C.-45° C. without affecting foaming property.

TABLE 3

| Description | Chemical names of components | Comparative Example 3 | Example 7 | Example 8 | Example 9 |
|---|---|---|---|---|---|
| Component a) | N-myristoyl L-aspartic acid docosyl ester | / | 1 | / | 2 |
| Component a) | N-myristoyl L-glutamic acid cetyl ester | / | 2 | / | 2 |
| Component a) | N-myristoyl L-glutamic acid stearyl ester | | | 0.2 | |
| Component a) | N-myristoyl L-glutamic acid docosyl ester | | | | 6 |
| Component b) | Docosanoic acid | / | 5 | / | 0.5 |
| Component b) | Mixture of lauric acid/myristic acid | / | 3 | 5 | / |
| Component b) | Palmitic acid | / | 1 | / | / |
| Component b) | Lauric acid | / | 0.5 | / | / |
| Component c) | Sodium cocoyl sarcosinate | 8 | 8 | 8 | 8 |
| Component c) | Coco amidopropyl betaine | 2 | 2 | 2 | 2 |
| Auxiliary material | Acrylate copolymer (trade name: Carbopol AQUA SF-1) | 15.0 | / | / | / |
| Auxiliary material | Potassium hydroxide | 1.0 | / | / | / |
| Component d) | Polyethylene glycol | 30 | 30 | 30 | 30 |
| Auxiliary materials | Preservative and essence | Proper amount | Proper amount | Proper amount | Proper amount |
| Component d) | Water | Balance | Balance | Balance | Balance |
| Viscosity at 5° C. (centipoise) | | 70280 | 33920 | 15240 | 29080 |
| Viscosity at 25° C. (centipoise) | | 27500 | 28400 | 12120 | 26100 |
| Viscosity at 45° C. (centipoise) | | 9060 | 25020 | 10620 | 22060 |
| Evaluation of foamability | | D | B | B | B |
| pH value | | 7.1 | 6.7 | 6.9 | 7.0 |

In Table 3, after an associating thickening component, acrylate copolymer, is added in Comparative Example 3, although the viscosity of the cleaning composition is improved, the viscosity of the cleaning composition varies greatly due to temperature effect, and serious fruit jelly appearance tends to occur especially at low temperature. Thus, the product has very poor foamability.

According to Examples 7-9 of the invention, after the components (a), (b), (c) and (d) of the invention are used in the cleaning composition, the cleaning composition not only exhibits higher viscosity, but also has relatively stable viscosity within the temperature range of 5° C.-45° C. without affecting foaming property.

TABLE 4

| Description | Chemical names of components | Comparative Example 4 | Example 10 | Example 11 | Example 12 |
|---|---|---|---|---|---|
| Component a) | N-palmitoyl L-aspartic acid cetyl ester | / | 2 | 5 | / |
| Component a) | N-palmitoyl L-aspartic acid stearyl ester | / | 1 | 2 | / |
| Component a) | N-palmitoyl L-aspartic acid docosyl ester | / | / | 3 | / |
| Component a) | N-palmitoyl L-glutamic acid cetyl ester | / | 2 | / | 1 |
| Component b) | Lauric acid | / | 5 | / | 5 |
| Component b) | Myristic acid | / | 2 | / | 5 |
| Component b) | Mixture of palmitic acid and stearic acid | / | / | 0.5 | 10 |
| Component b) | Stearic acid | / | 3 | / | / |
| Component c) | Sodium lauroyl glutamate | 15 | 15 | 15 | 15 |
| Component c) | Cocoamido hydroxysulfobetaine | 10 | 10 | 10 | 10 |
| Component c) | Cocinic acid monoisopropanolamide | 3 | 3 | 3 | 3 |
| Component d) | Sorbierite | 15 | 15 | 15 | 15 |
| Auxiliary materials | pH regulator, preservative and essence | Proper amount | Proper amount | Proper amount | Proper amount |
| Component d) | Water | Balance | Balance | Balance | Balance |
| Viscosity at 5° C. (centipoise) | | 35100 | 47080 | 43020 | 37580 |
| Viscosity at 25° C. (centipoise) | | 10500 | 41000 | 39820 | 34100 |
| Viscosity at 45° C. (centipoise) | | 5180 | 36140 | 34140 | 30800 |
| Evaluation of foamability | | B | B | A | A |
| pH value | | 6.9 | 7.0 | 6.8 | 7.0 |

In Table 4, the viscosity of the cleaning composition of Comparative Example 4 varies greatly due to temperature effect. According to Examples 10-12 of the invention, after the components (a), (b), (c) and (d) of the invention are used in the cleaning composition, the cleaning composition not only exhibits higher viscosity, but also has relatively stable viscosity within the temperature range of 5° C.-45° C. without affecting foaming property.

TABLE 5

| Description | Chemical names of components | Comparative Example 5 | Example 13 | Example 14 | Example 15 |
|---|---|---|---|---|---|
| Component a) | N-palmitoyl L-glutamic acid stearyl ester | / | 2 | 5 | / |
| Component a) | N-palmitoyl L-glutamic acid docosyl ester | / | 1 | 2 | / |
| Component a) | N-stearoyl L-aspartic acid cetyl ester | / | / | 3 | / |
| Component a) | N-stearoyl L-aspartic acid stearyl ester | / | 1.5 | / | 1 |
| Component a) | N-stearoyl L-aspartic acid docosyl ester | | 0.5 | | |
| Component b) | Lauric acid | / | 5 | / | 5 |
| Component b) | Myristic acid | / | 2 | / | 5 |
| Component b) | Palmitic acid | / | / | 0.5 | 10 |

TABLE 5-continued

| Description | Chemical names of components | Comparative Example 5 | Example 13 | Example 14 | Example 15 |
|---|---|---|---|---|---|
| Component b) | Glyceryl stearate (monoester content of more than 90%) | / | 3 | / | / |
| Component c) | Potassium cocoyl glycinate | 22 | 22 | 22 | 22 |
| Component c) | Lauryl amine oxide | 8 | 8 | 8 | 8 |
| Component c) | Cocinic acid monoethanolamide | 3 | 3 | 3 | 3 |
| Auxiliary material | PEG120 glucoside dioleate | 3 | / | / | / |
| Component d) | Ethanol | 5 | 5 | 5 | 5 |
| Auxiliary materials | Preservative and essence | Proper amount | Proper amount | Proper amount | Proper amount |
| Component d) | Water | Balance | Balance | Balance | Balance |
| Viscosity at 5° C. (centipoise) | | 34010 | 47020 | 40400 | 37280 |
| Viscosity at 25° C. (centipoise) | | 9880 | 42120 | 36080 | 34100 |
| Viscosity at 45° C. (centipoise) | | 6430 | 37200 | 30060 | 30880 |
| Evaluation of foamability | | D | A | A | A |
| pH value | | 7.0 | 7.0 | 6.7 | 7.0 |

In Table 5, the viscosity of the cleaning composition of Comparative Example 5 varies greatly due to temperature effect. According to Examples 13-15 of the invention, after the components (a), (b), (c) and (d) of the invention are used in the cleaning composition, the cleaning composition not only exhibits higher viscosity, but also has relatively stable viscosity within the temperature range of 5° C.-45° C. without affecting foaming property.

TABLE 6

| Description | Chemical names of components | Comparative Example 6 | Example 16 |
|---|---|---|---|
| Component a) | N-stearoyl L-glutamic acid cetyl ester | — | 0.5 |
| Component a) | N-stearoyl L-glutamic acid stearyl ester | — | 0.5 |
| Component a) | N-stearoyl L-glutamic acid docosyl ester | — | 1.0 |
| Component b) | Lauric acid | 2 | — |
| Component b) | Myristic acid | — | 3 |
| Component b) | Stearic acid | 5 | 7 |
| Component c) | Potassium monolauryl phosphate | — | 25 |
| Component c) | Sodium laurate | 20 | — |
| Component c) | Potassium stearate | 15 | — |
| Component c) | Coco amidopropyl betaine | 5 | 5 |
| Component d) | Sorbierite | 15 | 15 |
| Auxiliary materials | Preservative and essence | Proper amount | Proper amount |
| Component d) | Water | Balance | Balance |
| Viscosity at 5° C. (centipoise) | | 41140 | 35100 |
| Viscosity at 25° C. (centipoise) | | 34060 | 32800 |
| Viscosity at 45° C. (centipoise) | | 29180 | 30140 |
| Evaluation of foamability | | A | A |
| pH value | | 10.2 | 6.9 |

In Table 6, the cleaning composition partly saponified by fatty acids such as sodium laurate, potassium stearate and the like is used in Comparative Example 6. Although the product has better foaming property and viscosity change over temperature is also acceptable, pH value of the cleaning composition is about 10. Thus, strong basicity may lead to skin irritation problems for consumers. After the components (a), (b), (c) and (d) of the invention are used in the cleaning composition of Example 16, good foaming property and stable viscosity are also achieved, and pH value of the cleaning composition is neutral. Thus, the cleaning composition has smaller irritability and good safety.

TABLE 7

| Description | Chemical names of components | Example 17 | Example 18 | Example 19 | Example 20 |
|---|---|---|---|---|---|
| Component a) | N-lauroyl glutamic acid isotridecyl ester | 0.01 | 10 | 0.5 | 1 |
| Component a) | N-palmitoyl glutamic acid isotridecyl ester | — | 5 | — | — |
| Component a) | N-myristoyl aspartic acid isotridecyl ester | — | — | — | 1.5 |
| Component a) | N-stearoyl aspartic acid isotridecyl ester | — | 15 | — | 0.5 |
| Component b) | Lauric acid | — | 10 | 5 | 5 |

TABLE 7-continued

| Description | Chemical names of components | Example 17 | Example 18 | Example 19 | Example 20 |
|---|---|---|---|---|---|
| Component b) | Isostearic acid | 0.1 | 15 | 30 | 1.5 |
| Component b) | Trilaurin | — | 10 | 15 | 3 |
| Component c) | Sodium lauroyl sarcosinate | 65 | 1 | 11 | 18 |
| Component c) | Coco amidopropyl betaine | 5 | — | 1 | 5 |
| Component c) | Cocamide | 10 | — | 3 | 2 |
| Component d) | Maltitol | 5 | 5 | 5 | 5 |
| Auxiliary materials | Preservative and essence | Proper amount | Proper amount | Proper amount | Proper amount |
| Component d) | Water | Balance | Balance | Balance | Balance |
| Viscosity at 5° C. (centipoise) | | 37650 | 48710 | 42210 | 64210 |
| Viscosity at 25° C. (centipoise) | | 34400 | 45320 | 39800 | 62100 |
| Viscosity at 45° C. (centipoise) | | 32100 | 41200 | 36710 | 58910 |
| Evaluation of foamability | | A | C | B | A |
| pH value | | 7.0 | 6.8 | 6.6 | 7.0 |

In Table 7, according to Examples 17-20 of the invention, after the components (a), (b), (c) and (d) of the invention are used in the cleaning composition, the cleaning composition not only exhibits higher viscosity, but also has relatively stable viscosity within the temperature range of 5° C.-45° C. without affecting foaming property.

TABLE 8

| Description | Chemical names of components | Example 21 | Example 22 | Example 23 | Example 24 |
|---|---|---|---|---|---|
| Component a) | N-lauroyl L-glutamic acid isostearyl ester | 0.5 | 1 | 1.5 | — |
| Component a) | N-palmitoyl L-aspartic acid isostearyl ester | — | — | — | 0.2 |
| Component a) | N-myristoyl L-glutamic acid isostearyl ester | — | 1 | 1.5 | — |
| Component a) | N-stearoyl L-aspartic acid isostearyl ester | — | — | — | 0.5 |
| Component a) | N-myristoyl L-glutamic acid isododecyl ester | — | 2 | — | 0.1 |
| Component a) | N-stearoyl L-aspartic acid octyldodecyl ester | — | — | — | 0.5 |
| Component a) | N-lauroyl L-glutamic acid hexyldecyl ester | — | 1 | — | — |
| Component a) | N-palmitoyl L-aspartic acid octyldodecyl ester | — | — | 0.5 | — |
| Component b) | Isotridecanol | 2 | 3 | 2 | 3 |
| Component b) | Isostearic acid | 1 | — | — | 2 |
| Component b) | Lauric acid | 5 | 10 | 3 | 5 |
| Component b) | Glyeryl stearate | — | 7 | — | 5 |
| Component c) | Sodium myristoyl sarcosinate | 15 | 8 | 15 | 8 |
| Component c) | Sodium lauryl ether carboxylate | 3 | 2 | 3 | 2 |
| Component c) | Alkyl glycoside | 7 | 5 | 7 | 5 |
| Component d) | Sorbitol | 10 | 10 | 10 | 10 |
| Auxiliary materials | Preservative and essence | Proper amount | Proper amount | Proper amount | Proper amount |
| Component d) | Water | Balance | Balance | Balance | Balance |
| Viscosity at 5° C. (centipoise) | | 28640 | 48610 | 38280 | 35110 |
| Viscosity at 25° C. (centipoise) | | 26310 | 45310 | 36810 | 32060 |
| Viscosity at 45° C. (centipoise) | | 23500 | 41180 | 32640 | 29980 |
| Evaluation of foamability | | A | A | A | A |
| pH value | | 7.0 | 6.9 | 6.7 | 7.0 |

In Table 8, according to Examples 21-24 of the invention, after the components (a), (b), (c) and (d) of the invention are used in the cleaning composition, the cleaning composition not only exhibits higher viscosity, but also has relatively stable viscosity and good foaming effect within the temperature range of 5° C.-45° C.

Description of Stability Results:

The cleaning compositions of Examples 1-20 of the invention are placed respectively in 60° C. and 45° C. ovens as well as 5° C. and −15° C. refrigerators. Six months later, state of the materials is visually observed, and there are no phase separation and other changes. The viscosity of the cleaning compositions of Examples 1-20 at 5° C., 25° C. and 45° C. is retested, showing that the result has no obvious change compared with that prior to placement. See Table 9 for details of the viscosity test results.

TABLE 9

|  | Example 1 | | Example 2 | | Example 3 | | Example 4 | |
| --- | --- | --- | --- | --- | --- | --- | --- | --- |
|  | Initial | Retest | Initial | Retest | Initial | Retest | Initial | Retest |
| Viscosity at 5° C. (centipoise) | 34500 | 34480 | 51040 | 51020 | 47400 | 47300 | 49020 | 49000 |
| Viscosity at 25° C. (centipoise) | 32020 | 32020 | 45080 | 45100 | 41200 | 41200 | 44120 | 44110 |
| Viscosity at 45° C. (centipoise) | 30160 | 30200 | 42200 | 42180 | 38100 | 38110 | 39200 | 39300 |

|  | Example 5 | | Example 6 | | Example 7 | | Example 8 | |
| --- | --- | --- | --- | --- | --- | --- | --- | --- |
|  | Initial | Retest | Initial | Retest | Initial | Retest | Initial | Retest |
| Viscosity at 5° C. (centipoise) | 42460 | 42500 | 36880 | 36900 | 33920 | 34000 | 15240 | 15240 |
| Viscosity at 25° C. (centipoise) | 38100 | 38080 | 33100 | 33100 | 28400 | 28410 | 12120 | 12120 |
| Viscosity at 45° C. (centipoise) | 32080 | 32100 | 29600 | 29640 | 25020 | 25000 | 10620 | 10640 |

|  | Example 9 | | Example 10 | | Example 11 | | Example 12 | |
| --- | --- | --- | --- | --- | --- | --- | --- | --- |
|  | Initial | Retest | Initial | Retest | Initial | Retest | Initial | Retest |
| Viscosity at 5° C. (centipoise) | 29080 | 29100 | 47080 | 47040 | 43020 | 43080 | 37580 | 37600 |
| Viscosity at 25° C. (centipoise) | 26100 | 26100 | 41000 | 41020 | 39820 | 39810 | 34100 | 34110 |
| Viscosity at 45° C. (centipoise) | 22060 | 22000 | 36140 | 36180 | 34140 | 34100 | 30800 | 30820 |

|  | Example 13 | | Example 14 | | Example 15 | | Example 16 | |
| --- | --- | --- | --- | --- | --- | --- | --- | --- |
|  | Initial | Retest | Initial | Retest | Initial | Retest | Initial | Retest |
| Viscosity at 5° C. (centipoise) | 47020 | 47000 | 40400 | 40410 | 37280 | 37300 | 35100 | 35110 |
| Viscosity at 25° C. (centipoise) | 42120 | 42120 | 36080 | 36100 | 34100 | 34110 | 32800 | 32800 |
| Viscosity at 45° C. (centipoise) | 37200 | 37220 | 30060 | 30080 | 30880 | 30900 | 30140 | 30140 |

|  | Example 17 | | Example 18 | | Example 19 | | Example 20 | |
| --- | --- | --- | --- | --- | --- | --- | --- | --- |
|  | Initial | Retest | Initial | Retest | Initial | Retest | Initial | Retest |
| Viscosity at 5° C. (centipoise) | 37650 | 37660 | 48710 | 48700 | 42210 | 42220 | 64210 | 64200 |
| Viscosity at 25° C. (centipoise) | 34400 | 34400 | 45320 | 45340 | 39800 | 39820 | 62100 | 62100 |

TABLE 9-continued

| Viscosity at 45° C. (centipoise) | 32100 | 32180 | 41200 | 41210 | 36710 | 36700 | 58910 | 58900 |
|---|---|---|---|---|---|---|---|---|

| | Example 21 | | Example 22 | | Example 23 | | Example 24 | |
|---|---|---|---|---|---|---|---|---|
| | Initial | Retest | Initial | Retest | Initial | Retest | Initial | Retest |
| Viscosity at 5° C. (centipoise) | 28640 | 28600 | 48610 | 48610 | 38280 | 38300 | 35110 | 35100 |
| Viscosity at 25° C. (centipoise) | 26310 | 26320 | 45310 | 45300 | 36810 | 36850 | 32060 | 32100 |
| Viscosity at 45° C. (centipoise) | 23500 | 23550 | 41180 | 41200 | 32640 | 32600 | 29980 | 30000 |

All the documents mentioned in the invention are cited as references in the application, just as the same document is cited alone as reference. Additionally, it should be understood that those skilled in the art can make various changes or modifications to the invention after reading the above teachings of the invention, and these equivalents also fall into the scope defined by the appended claims of the application.

The invention claimed is:

1. A thick cleaning composition, the thick cleaning composition comprising the following components (a), (b), (c) and (d):
    a component (a): a long-chain fatty acyl acidic amino acid ester, N-palmitoyl L-aspartic isotridecyl ester, which accounts for 0.01%-30% of the cleaning composition based on weight percentage;
    a component (b): a fatty compound, trilaurin, which accounts for 0.1%-50% of the cleaning composition based on weight percentage;
    a component (c): one or more surfactants, which account for 1%-80% of the cleaning composition based on weight percentage; and
    a component (d): a solvent composed of one or more substances selected from water, lower alcohols, polyols and polyol ethers, which accounts for 10%-90% of the cleaning composition based on weight percentage.

2. The thick cleaning composition according to claim 1, wherein the composition is a surfactant lyotropic liquid crystal.

3. The thick cleaning composition according to claim 2, wherein the composition comprises at least one of a lamellar liquid crystal, a hexagonal liquid crystal and a cubic liquid crystal.

4. The thick cleaning composition according to claim 1, wherein the component (a), the long-chain fatty acyl acidic amino acid ester, accounts for 0.1-20% of the cleaning composition based on weight percentage.

5. The thick cleaning composition according to claim 4, wherein the component (a), the long-chain fatty acyl acidic amino acid ester, accounts for 0.2-10% of the cleaning composition based on weight percentage.

6. The thick cleaning composition according to claim 5, wherein the component (a), the long-chain fatty acyl acidic amino acid ester, accounts for 0.5-3% of the cleaning composition based on weight percentage.

7. The thick cleaning composition according to claim 1, wherein the component (b), the fatty compound, accounts for 0.1%-35% of the cleaning composition based on weight percentage.

8. The thick cleaning composition according to claim 7, wherein the component (b), the fatty compound, accounts for 0.5%-20% of the cleaning composition based on weight percentage.

9. The thick cleaning composition according to claim 1, wherein the component (c), the one or more surfactants, are selected from anionic surfactants, zwitterionic surfactants, nonionic surfactants and cationic surfactants or a mixture thereof.

10. The thick cleaning composition according to claim 9, wherein the component (c), the one or more surfactants, are an anionic surfactant.

11. The thick cleaning composition according to claim 1, wherein the component (c), the one or more surfactants, accounts for 5-50% of the cleaning composition based on weight percentage.

12. The thick cleaning composition according to claim 11, wherein the component (c), the one or more surfactants, accounts for 10-40% of the cleaning composition based on weight percentage.

13. The thick cleaning composition according to claim 12, wherein the component (c), the one or more surfactants, accounts for 15-25% of the cleaning composition based on weight percentage.

14. The thick cleaning composition according to claim 1, wherein the component (d), the solvent, accounts for 35-80% of the cleaning composition based on weight percentage.

15. The thick cleaning composition according to claim 1, wherein the component (d), the solvent, accounts for 55-80% of the cleaning composition based on weight percentage.

16. The thick cleaning composition according to claim 1, wherein viscosity of the thick cleaning composition is more than 10,000 cps.

17. The thick cleaning composition according to claim 1, wherein the cleaning composition further comprises at least one of the following beautifying and cleaning adjuvants for skin, eyes, teeth and hair, which is selected from rheology modifiers, humectants, polymers, superfatting agents, saccharides, inorganic powder, organic powder, siloxane, pearlescing agents, pH regulators, opacifiers, active ingredients, preservatives, chelating agents, antimicrobial agents, antioxidants, dye or essence.

18. The thick cleaning composition according to claim 1, wherein the thick cleaning composition is used for cleaning skin, eyes, teeth and hair.

* * * * *